United States Patent [19]

Rossetti et al.

[11] 4,175,077

[45] * Nov. 20, 1979

[54] RIFAMYCIN COMPOUNDS

[75] Inventors: Vittorio Rossetti; Leonardo Marsili; Carmine Pasqualucci, all of Milan, Italy

[73] Assignee: ARCHIFAR Industrie Chimiche del Trentino S.p.A., Rovereto, Italy

[ * ] Notice: The portion of the term of this patent subsequent to Apr. 12, 1994, has been disclaimed.

[21] Appl. No.: 825,163

[22] Filed: Aug. 12, 1977

[30] Foreign Application Priority Data

Sep. 30, 1976 [IT] Italy ................................ 5209 A/76

[51] Int. Cl.$^2$ ......................................... C07D 498/08
[52] U.S. Cl. ............................ 260/239.3 P; 424/244
[58] Field of Search .................................. 260/239.3 P

[56] References Cited

U.S. PATENT DOCUMENTS 4,017,481   4/1977   Marsili et al. ................. 260/239.3 P

FOREIGN PATENT DOCUMENTS 1670479   1/1971   Fed. Rep. of Germany .... 260/239.3 P
1670377   2/1974   Fed. Rep. of Germany .... 260/239.3 P
2620782  11/1976   Fed. Rep. of Germany .... 260/239.3 P

*Primary Examiner*—John M. Ford
*Assistant Examiner*—Robert T. Bond
*Attorney, Agent, or Firm*—Haseltine, Lake & Waters

[57] ABSTRACT

Rifamycin compounds having high antibacterial activity, comprising derivatives of 3-aminosubstituted-4-desoxo-4-imino rifamycin S. These compounds are powders of red violet color and are provided by reacting 3-aminosubstituted rifamycin S with ammonia gas.

1 Claim, No Drawings

RIFAMYCIN COMPOUNDS

This invention relates to novel rifamycin compounds having anti-bacterial activity.

In German Patent Application DOS 1,670,479 laid open Jan. 28, 1971 and in German Patent specification No. 1,670,377 granted Feb. 28, 1974, derivatives of rifamycin S are described as having the formula:

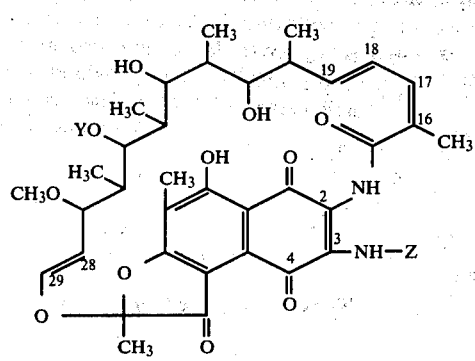

and 16, 17, 18, 19 tetrahydroderivatives and 16, 17, 18, 19, 28, 29 hexahydroderivatives thereof, wherein:

Y is —H or —COCH$_3$, and Z is, inter alia, an alkyl having 1 to 4 C atoms; cycloalkyl having 3 to 6 C atoms; phenyl; phenyl substituted with at least one radical selected from the group comprising halogen, methyl and hydroxy.

In German Patent Application DOS 2,620,782 laid open Nov. 25, 1976, compounds of formula similar to formula (I) are described, but distinct therefrom in that a —NH$_2$ group is bonded to C atom at position 3 of the molecule and a group =NH is bonded to C atom at position 4. This invention is concerned with novel rifamycin compounds having the formula

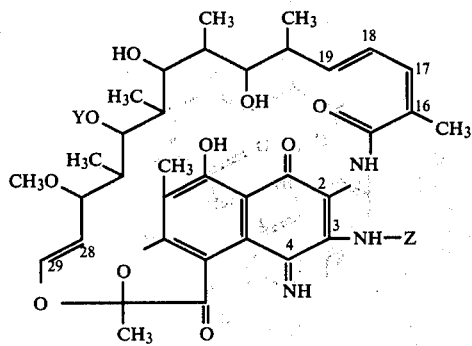

and 16, 17, 18, 19 tetrahydroderivatives and 16, 17, 18, 19, 28 29 hexahydroderivatives thereof, where Y and Z are as above defined for formula (I), and it also relates to the reduced compounds of formula (II), having in turn the formula:

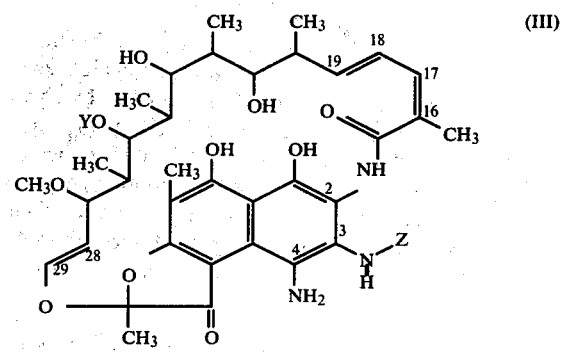

and 16, 17, 18, 19 tetrahydroderivatives and 16, 17, 18, 19, 28, 29 hexhydroderivatives thereof, wherein Y and Z are as above defined.

These compounds are of red violet colour and exhibit high antibacterial activity.

The compounds of formula (II) are obtained by reacting ammonia gas with the compounds of formula (I) dissolved in an aprotic solvent selected from the group comprising tetrahydrofuran and 1,4-dioxane, at a temperature in the range of $-10°$ C.$-+35°$ C.

In order that the present invention be more clearly understood, some exemplary embodiments thereof will now be illustrated as given by way of unrestricted example.

Chromatography studies on thin layer are effected on Merck F$_{254}$ plates 5×10 cm, using as eluent a mixture chloroform/ethyl acetate/methanol (10:2:0.5).

EXAMPLE 1

13.3 g 3-cyclopropylamino-rifamycin S were dissolved in 130 ml tetrahydrofuran; the solution was cooled to $+10°$ C. and anhydrous ammonia was blown in for 4 hours. Excess ammonia was removed under vacuum at $+10°$ C. and the reaction mixture diluted with 300 ml chloroform, then pouring into water and maintaining pH 7 with citric acid. The product was decanted, the organic layer dried on sodium sulphate and concentrated to small volume at reduced pressure. Thus, 3-cyclopropylamino-4-desoxo-4-imino-rifamycin S crystallized in red crystals; yield 7.1 g.

Rf=0.47

I.R. 3450, 3275-3175, 1740, 1705, 1640, 1610, 1590(Sh), 1560, 1520, 1420, 1320, 1295, 1250, 1210, 1175, 1140, 1120, 1080, 965, 945, 895, 835 and 810 cm$^-$.

mp. 140°-145° C. (dec.)

$\lambda_{max}$ (methanol)=490 nm (E$_{1\ cm}$ $^{1\%}$=29.6), 320 nm (E$_{1\ cm}$$^{1\%}$=159), 264 nm (E$_{1\ cm}$$^{1\%}$=382).

$^{13}$C NMR in C$_6$D$_6$ shows a peak at 158.1 p.p.m. (by using TMS as internal reference) ascribed to C-4.

| Elementary analysis for: C$_{40}$H$_{51}$N$_3$O$_{11}$: | | | |
|---|---|---|---|
| | C | H | N |
| Calculated (%): | 64.07 | 6.86 | 5.60 |
| Found (%): | 64.42 | 6.57 | 5.55 |

EXAMPLE 2

5 g 3-orthololuidino rifamycin S were dissolved in 50 ml tetrahydrofuran; the solution was cooled to 0° C. and ammonia gas was blown in for 10 minutes. The reaction mixture was allowed to rest at 0° C. for 2 hours, excess ammonia was removed under vacuum, then concentrating to small volume, so that by addition of cyclohexane the raw product precipitated and was purified by chromatography on column filled up with 250 g silica gel, and by eluting with benzene and a gradient of methanol in the range of 0.5–2.5%; the eluate containing pure product was dry concentrated at reduced pressure, then crystallizing from benzene. 1.75 g 3-orthotoluidino 4-desoxo 4-imino-rifamycin S in red crystals were obtained.

Rf=0.55

I.R. 3350(B), 1720, 1655, 1610, 1580(Sh), 1525, 1310, 1265, 1220, 1170, 1130, 1080, 980, 950 and 820 cm$^{-1}$.

| Elementary analysis for: $C_{44}H_{53}N_3O_{11}$: | | | |
|---|---|---|---|
| | C | H | N |
| Calculated (%): | 66.07 | 6.68 | 5.25 |
| Found (%): | 66.59 | 6.58 | 5.08 |

$\lambda_{max}$ (CHCl$_3$)=524 nm (E$_1$ $_{cm}$$^{1\%}$=65.8), 327 nm (E$_1$ $_{cm}$$^{1\%}$=387), 244 nm (E$_1$ $_{cm}$$^{1\%}$=313).

EXAMPLE 3

5 g 3-chloroanilino-rifamycin S were dissolved in 50 ml tetrahydrofuran, the solution was cooled to +3° C. and anhydrous ammonia was blown in for 5 minutes, temperature was allowed to rise to room temperature and after 12 hours anhydrous ammonia was blown in for 2 minutes. The solution was allowed to rest for 2 hours and excess ammonia was removed under vacuum, then diluting with 200 ml dichloromethane and repeatedly washing with 5% aqueous solution of citric acid.

After drying and dry evaporation at reduced pressure, the raw residue was purified by chromatography on column as described in Example 2, obtaining 1.8 g 3-p-chloroanilino-4-desoxo-4-imino-rifamycin S in red crystals.

Rf=0.68.

EXAMPLE 4

6 g 3-propylamino-rifamycin S were dissolved in 60 ml tetrahydrofuran and cooled to 0° C. Then, anhydrous ammonia was blown in for 8 hours. After overnight rest at +5° C., excess ammonia was removed under vacuum, then diluting with 200 ml dichloromethane and washing the solution with 5% aqueous solution of citric acid. As decanted and separated, the organic layer was dried on sodium sulphate and evaporated to dryness at reduced pressure. The residue was chromatographed on column as described in Example 2, thus obtaining 1.5 g 3-propylamino-4-desoxo-4-imino-rifamycin in red crystals.

Rf=0.48

EXAMPLE 5

A solution of 3 g 3-cyclohexylamino-rifamycin S dissolved in 50 ml tetrahydrofuran was subjected to a slow but continuous flow of ammonia gas at +5° C. for 4 days. Excess ammonia was removed under vacuum and the solvent was dry evaporated at reduced pressure. A residue was obtained, which when chromatographed on column as described in Example 2 yielded 2 g 3-cyclohexylamino-4-desoxo-4-imino-rifamycin S in red crystals.

Rf=0.50.

EXAMPLE 6

A solution of 5 g 3-anilino-rifamycin S dissolved in 50 ml tetrahydrofuran was subjected to a flow of anhydrous ammonia at 0° C. for 10 minutes. The reaction mixture was allowed to rest at room temperature for 2 hours. Excess ammonia was removed under vacuum, then diluting with 200 ml chloroform and washing with 5% aqueous solution of citric acid. The organic layer, as dried on sodium sulphate, was dry evaporated at reduced pressure. The raw product thus provided was purified by chromatography on column as described in Example 2. Thus, 1.3 g 3-anilino-4-desoxo-4-imino-rifamycin S in red crystals were obtained.

Rf=0.65.

I.R. 3370, 3120, 1720, 1650(B), 1615, 155, 1410, 1305, 1260, 1215, 1182, 1170, 1145, 1130, 1080, 980, 950, 928, 870 and 825 cm$^{-1}$.

What we claim is:

1. A rifamycin compound having the formula:

(II)

and 16, 17, 18, 19 tetrahydroderivatives and 16, 17, 18, 19, 28, 29 hexahydroderivatives thereof, wherein:

Y is —H or —COCH$_3$ and Z is an alkyl having 1 to 4 C atoms; cycloalkyl having 3 to 6 C atoms; phenyl; phenyl substituted with one radical selected from the group consisting of halogen, methyl and hydroxy; and corresponding reduced compounds of formula:

(III)

and 16, 17, 18, 19 tetrahydroderivatives and 16, 17, 18 , 19, 28, 29 hexahydroderivatives thereof, wherein Y and Z are as above defined.

* * * * *